US010212780B2

(12) United States Patent
Machida

(10) Patent No.: US 10,212,780 B2
(45) Date of Patent: Feb. 19, 2019

(54) LIGHT SOURCE DEVICE

(71) Applicant: OLYMPUS CORPORATION, Hachioji-shi, Tokyo (JP)

(72) Inventor: Ryo Machida, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/004,047

(22) Filed: Jun. 8, 2018

(65) Prior Publication Data

US 2018/0295682 A1 Oct. 11, 2018

Related U.S. Application Data

(63) Continuation of application No. PCT/JP2016/083283, filed on Nov. 9, 2016.

(30) Foreign Application Priority Data

Dec. 14, 2015 (JP) .................................. 2015-243140

(51) Int. Cl.
*A61B 1/06* (2006.01)
*A61B 1/07* (2006.01)
(Continued)

(52) U.S. Cl.
CPC .............. *H05B 33/086* (2013.01); *A61B 1/06* (2013.01); *G02B 23/2469* (2013.01);
(Continued)

(58) Field of Classification Search
None
See application file for complete search history.

(56) References Cited

U.S. PATENT DOCUMENTS

2011/0208004 A1 8/2011 Feingold et al.
2016/0231494 A1 8/2016 Feingold et al.
(Continued)

FOREIGN PATENT DOCUMENTS

EP 3050492 A1 8/2016
JP H11205806 A 7/1999
(Continued)

OTHER PUBLICATIONS

International Search Report (ISR) dated Jan. 24, 2017 issued in International Application No. PCT/JP2016/083283.
(Continued)

*Primary Examiner* — Dedei K Hammond
(74) *Attorney, Agent, or Firm* — Holtz, Holtz & Volek PC

(57) ABSTRACT

A light source device is provided with: a plurality of surface light sources that have different wavelength bands; a multiplexing unit that multiplexes light beams emitted from the surface light sources; and an adjustment unit that adjusts, when an endoscope that serves as a reference endoscope is connected, the light amounts of light beams emitted from the surface light sources such that illumination light emitted from the reference endoscope has a predetermined color balance and that corrects, when an arbitrary endoscope is connected, the color balance on the basis of the ratio of the color balance of illumination light emitted from the connected endoscope and the color balance of illumination light emitted from the reference endoscope.

6 Claims, 3 Drawing Sheets

(51) Int. Cl.
- *H05B 33/08* (2006.01)
- *G02B 23/26* (2006.01)
- *G02B 23/24* (2006.01)
- *G02B 27/14* (2006.01)

(52) U.S. Cl.
CPC ......... *G02B 23/26* (2013.01); *H05B 33/0872* (2013.01); *G02B 27/141* (2013.01)

(56) References Cited

U.S. PATENT DOCUMENTS

2016/0235285 A1   8/2016   Shirota et al.
2017/0272720 A1*  9/2017   Oki ..................... H05B 37/02

FOREIGN PATENT DOCUMENTS

| JP | 2001208986 A | 8/2001 |
| JP | 2002238846 A | 8/2002 |
| JP | 4447520 B2 | 4/2010 |
| JP | 2011224044 A | 11/2011 |
| JP | 2012509098 A | 4/2012 |
| WO | 2015064470 A1 | 5/2015 |

OTHER PUBLICATIONS

Written Opinion dated Jan. 24, 2017 issued in International Application No. PCT/JP2016/083283.

* cited by examiner

LIGHT SOURCE DEVICE

CROSS-REFERENCE TO RELATED APPLICATIONS

This is a continuation of International Application PCT/JP2016/083283 which is hereby incorporated by reference herein in its entirety.

This application is based on Japanese Patent Application No. 2015-243140, the contents of which are incorporated herein by reference.

TECHNICAL FIELD

The present invention relates to a light source device.

BACKGROUND ART

In the related art, there is a known light source device in which light beams output from a plurality of LED light sources and having different wavelengths are multiplexed and are introduced to an optical transmission rod, and the multiplexed light transmitted through the optical transmission rod is emitted (for example, see PTL 1). The light emitted from the light source device is made to enter an optical fiber cable in an endoscope and is used as illumination light.

In the light source device of PTL 1, part of the multiplexed light output from the optical transmission rod is extracted and is detected by a color sensor, and the color balance of the light beams from the respective LED light sources is adjusted by a color-balance circuit.

CITATION LIST

Patent Literature

{PTL 1} Japanese Translation of PCT International Application, Publication No. 2012-509098

SUMMARY OF INVENTION

According to one aspect, the present invention provides a light source device including: a plurality of surface light sources having different wavelength bands; a multiplexing unit that multiplexes light beams emitted from the surface light sources; and an adjustment unit that adjusts, when an endoscope that serves as a reference endoscope is connected, light-emission amounts of the surface light sources such that illumination light emitted from the reference endoscope has a predetermined color balance, and that corrects, when an arbitrary endoscope is connected, the color balance on the basis of the ratio of the color balance of illumination light emitted from the connected endoscope and the color balance of illumination light emitted from the reference endoscope.

DESCRIPTION OF EMBODIMENTS

A light source device 1 according to one embodiment of the present invention will be described below with reference to the drawings.

Figure 1:
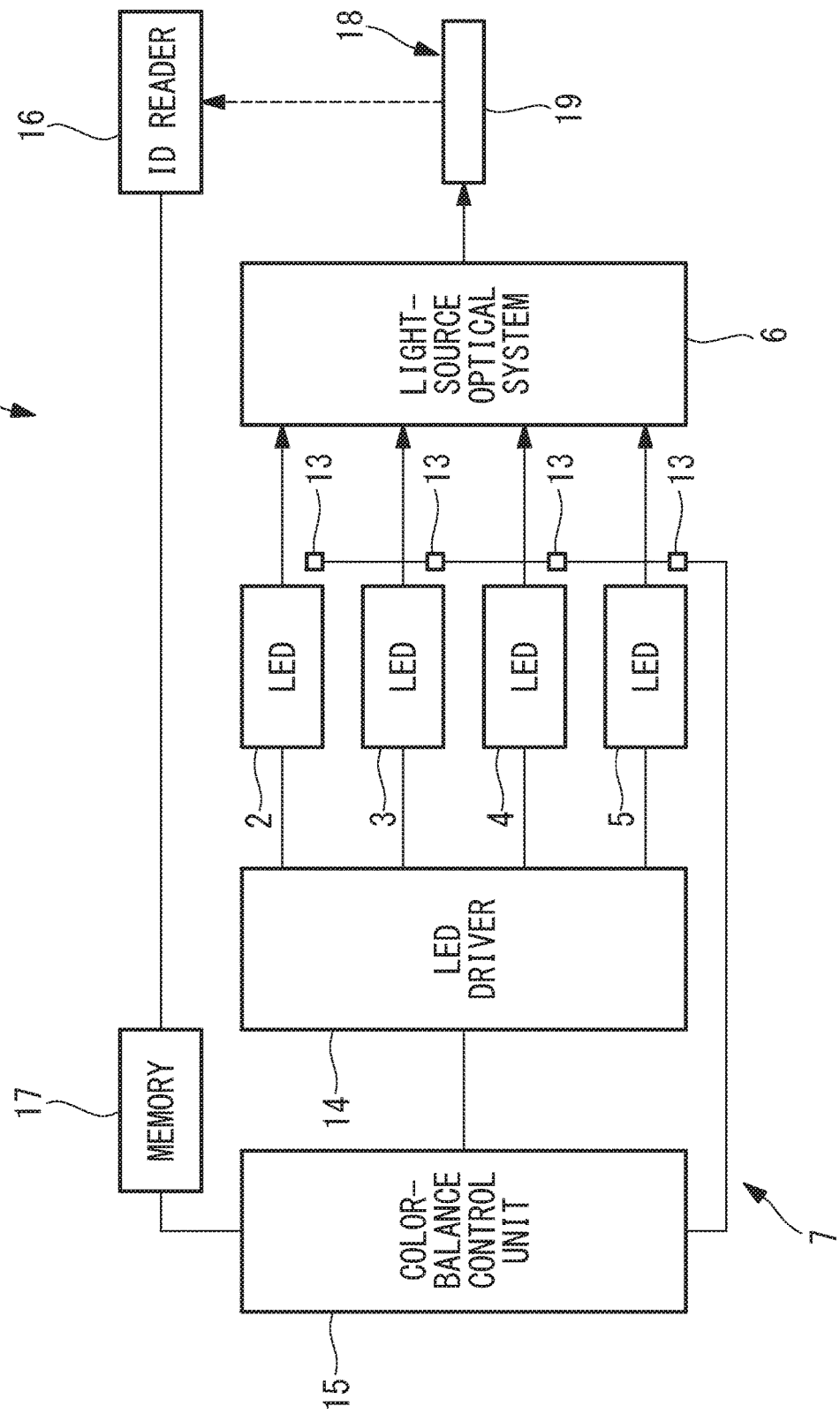
FIG. 1 is a block diagram showing a light source device according to one embodiment of the present invention.

As shown in FIG. 1, the light source device 1 of this embodiment is provided with: a plurality of LEDs (surface light sources) 2, 3, 4, and 5; a light-source optical system (multiplexing unit) 6; and an adjustment unit 7. The plurality of LEDs emit light beams in different wavelength bands. The light-source optical system 6 multiplexes the light beams from the plurality of LEDs 2, 3, 4, and 5. The adjustment unit 7 adjusts the color balance of the light beams emitted from the respective LEDs 2, 3, 4, and 5.

Figure 2:
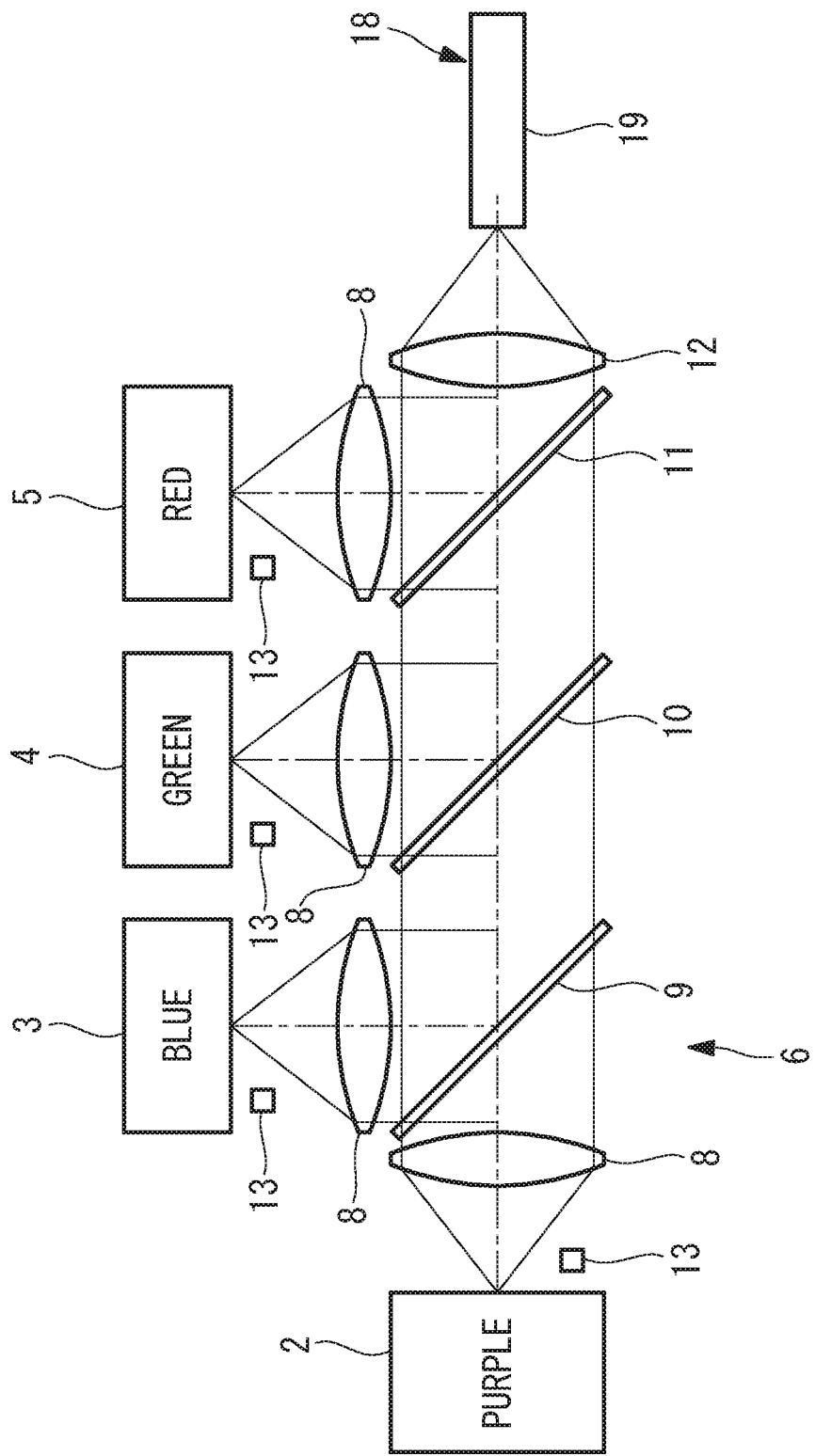
FIG. 2 is a schematic view showing surface light sources and a light-source optical system that are provided in the light source device shown in FIG. 1.

As shown in FIG. 2, the LEDs 2, 3, 4, and 5 are the purple LED 2, the blue LED 3, the green LED 4, and the red LED 5.

As shown in FIG. 2, the light-source optical system 6 is provided with: collimating lenses 8 that convert light beams from the LEDs 2, 3, 4, and 5 into approximately collimated beams; three dichroic filters 9, 10, and 11; and a focusing lens 12.

In the example shown in FIG. 2, light beams that are emitted from the purple LED 2 and the blue LED 3 and that are converted into approximately collimated light beams by the corresponding collimating lenses 8 are multiplexed by the first dichroic filter 9. Furthermore, the light beams multiplexed by the first dichroic filter 9 and a light beam that is emitted from the green LED 4 and that is converted into an approximately collimated light beam by the corresponding collimating lens 8 are multiplexed by the second dichroic filter 10.

Furthermore, the light beams multiplexed by the second dichroic filter 10 and a light beam that is emitted from the red LED 5 and that is converted into an approximately collimated light beam by the corresponding collimating lens 8 are multiplexed by the third dichroic filter 11.

Figure 3:
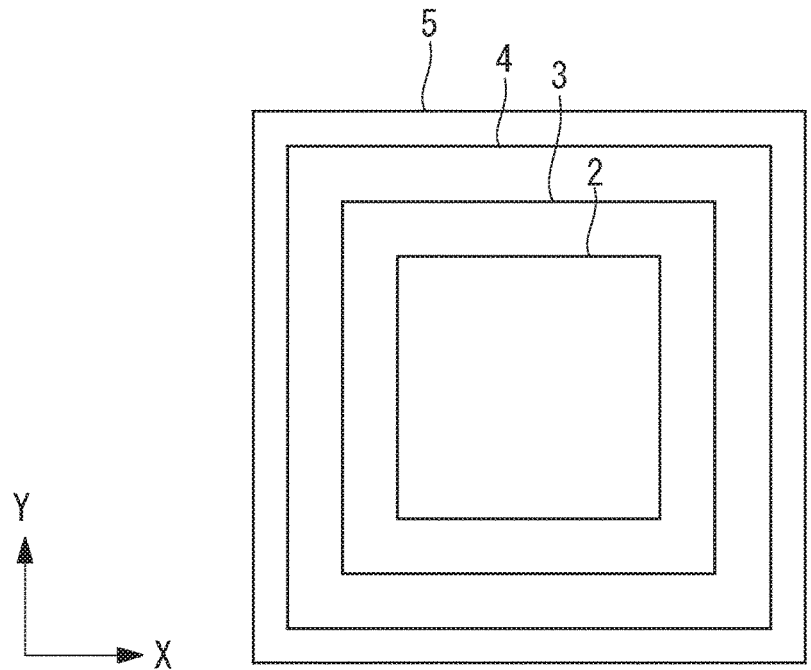
FIG. 3 is a plan view showing the sizes of light-emitting surfaces of the respective surface light sources in the light source device shown in FIG. 1.

In this embodiment, as shown in FIG. 3, the respective LEDs 2, 3, 4, and 5 have square light-emitting surfaces, and the light-emitting areas of the light-emitting surfaces have sizes in the following order: red LED 5>green LED 4>blue LED 3>purple LED 2.

Furthermore, the LEDs 2, 3, 4, and 5 each have a predetermined effective irradiation angle centered on the central axis of the light-emitting surface, and illumination light within the effective irradiation angle is converted into approximately collimated light by the corresponding collimating lens 8. Then, as shown in FIG. 2, the LEDs 2, 3, 4, and 5 are each provided with a sensor 13 that detects the color balance of light emitted toward the outside of the effective irradiation angle.

The adjustment unit 7 is provided with an LED driver 14 that controls the light-emission amounts of the four LEDs 2, 3, 4, and 5 and a color-balance control unit (adjustment unit) 15 that instructs the LED driver 14 to control the light-emission amounts of the respective LEDs 2, 3, 4, and 5.

Furthermore, the light source device 1 of this embodiment is provided with: an ID reader (detection unit) 16 that reads identification information stored in an ID chip provided on an endoscope 18 to be connected; and a memory (storage unit) 17 that stores identification information and correction values in an associated manner.

The ID reader 16 detects the type of the endoscope 18 from the identification information read from the ID chip.

The correction values are values for changing the light-emission amounts of the respective LEDs 2, 3, 4, and 5 when a different type of endoscope is connected. The correction values are set, for example, with reference to the light-emission amounts of the LEDs 2, 3, 4, and 5 that achieve a predetermined color balance when an endoscope 18 including a light guide 19 that serves as a reference light guide is connected.

In this embodiment, the correction values are set as follows.

Figure 4:
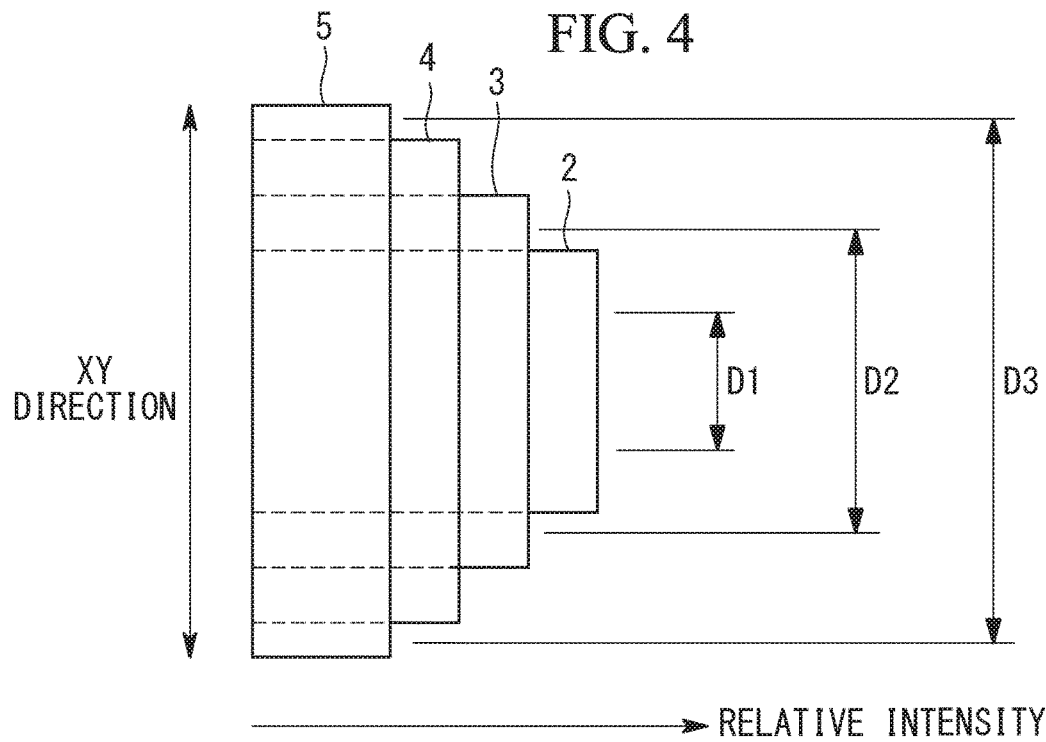
FIG. 4 is a view showing the relative intensities of the respective surface light sources in the light source device shown in FIG. 1.

Specifically, as shown in FIG. 4, in a case in which the diameter of the light guide 19 serving as a reference light guide is D2, when an endoscope 18 that includes a light guide 19 whose diameter is D2 is connected, the correction values are set to 1. That is, the color-balance control unit 15 controls the LED driver 14 such that the respective LEDs 2, 3, 4, and 5 emit, to the reference light guide 19, reference light-emission amounts of light beams that achieve a set color balance.

On the other hand, in a case in which the diameter of a light guide 19 in the connected endoscope 18 is D1 (<D2), because the light amounts from the green LED 4 and the red LED 5, which are larger than the diameter D2, are reduced compared with the case of the reference light guide 19. Thus, correction values for increasing the light-emission amounts of the LEDs 4 and 5 are set.

Furthermore, in a case in which the diameter of a light guide 19 in the connected endoscope 18 is D3 (>D2), the light amounts from the green LED 4 and the red LED 5, which are larger than the diameter D2, are increased, thus causing a yellowish color balance as illumination light. Therefore, correction values for increasing the light-emission amounts of the purple LED 2 and the blue LED 3, which have smaller light-emitting areas than the diameter D2 of the reference light guide 19, are set.

According to the thus-configured light source device 1 of this embodiment, because the endoscope 18 to be connected is identified with the identification information read by the ID reader 16, and the light-emission amounts from the respective LEDs 2, 3, 4, and 5 are corrected by the correction values corresponding to the endoscope 18. Therefore, there is an advantage in that, even when a different endoscope is connected, the color balance of illumination light emitted from the distal end of the endoscope can be adjusted at a constant level.

Furthermore, in this embodiment, because the sensors 13 detect, of light emitted from the LEDs 2, 3, 4, and 5, light emitted toward the outside of the effective irradiation angle range, there is an advantage in that light used for illumination is not lost, thus making it possible to efficiently use produced light for illumination.

In this embodiment, although a description has been given of a case in which the four LEDs 2, 3, 4, and 5 are used, instead of this, the present invention can be applied to a case in which two LEDs, three LEDs, or five or more LEDs are used.

Furthermore, although a description has been given of a case in which the diameter D2, which has an intermediate size, is used as the diameter of the reference light guide 19, instead of this, it is also possible to set the diameter of the reference light guide 19 to the smallest diameter D1, and to adopt correction values for increasing the light-emission amount of the purple LED 2, the blue LED 3 or the green LED 4, as the diameter of the light guide 19 in the connected endoscope 18 is increased.

In this embodiment, although the correction values are stored in the memory 17, it is also possible to further provide a calculation unit (not shown) that calculates the area ratio of an incident end of a light guide 19 in the endoscope 18 and an incident end of the reference light guide 19, to calculate the area ratio of the light guides 19 every time by means of the calculation unit, and to calculate correction values on the basis of the calculated area ratio.

In this embodiment, although the light-emission amounts of the respective LEDs 2, 3, 4, and 5 are corrected according to the area ratio of the light guides 19, instead of this, it is also possible to store, in the memory 17, correction values based on the ratio of the light-emission amount from the distal end of a reference endoscope 18 when the reference endoscope 18 is connected and the light-emission amount from the distal end of each endoscope 18 when the endoscope 18 is connected, and to read correction values according to the type of the connected endoscope 18, for correction.

By doing so, it is possible to correct variations in color balance caused not only by the diameter of the light guide 19 but also by a variation in the length of an insertion portion, etc.

The above-described embodiment leads to the following inventions.

According to one aspect, the present invention provides a light source device including: a plurality of surface light sources having different wavelength bands; a multiplexing unit that multiplexes light beams emitted from the surface light sources; and an adjustment unit that adjusts, when an endoscope that serves as a reference endoscope is connected, light-emission amounts of the surface light sources such that illumination light emitted from the reference endoscope has a predetermined color balance, and that corrects, when an arbitrary endoscope is connected, the color balance on the basis of the ratio of the color balance of illumination light emitted from the connected endoscope and the color balance of illumination light emitted from the reference endoscope.

According to this aspect, light beams in different wavelength bands produced by the plurality of surface light sources are multiplexed by the multiplexing unit. The light amounts of the light beams produced by the surface light sources are adjusted by the adjustment unit so as to have a predetermined color balance when an endoscope that serves as a reference endoscope is connected, and are emitted. When an arbitrary endoscope that is different from the reference endoscope is connected, the adjustment unit corrects the light-emission amounts of the respective surface light sources on the basis of the ratio of the color balance of illumination light emitted from the connected endoscope and the color balance of illumination light emitted from the reference endoscope. Accordingly, even when a different endoscope is connected, the color balance of illumination light emitted from the distal end of the endoscope can be adjusted to a constant level.

The above-described aspect may further include a storage unit that stores correction values based on the ratio of the color balance of illumination light emitted from the reference endoscope and the color balance of illumination light emitted from the connected endoscope, wherein the adjustment unit may correct the color balance on the basis of the correction values stored in the storage unit.

By doing so, because the correction values corresponding to the connected endoscope are read from the storage unit, and the color balance is corrected, even when a different endoscope is connected, illumination light emitted from the distal end of the endoscope can be easily and rapidly made into illumination light having a predetermined color balance.

In the above-described aspect, the adjustment unit may correct the color balance on the basis of the ratio of the area of an incident end of a light guide provided in the reference endoscope and the area of an incident end of a light guide provided in the connected endoscope.

By doing so, even when the area ratio of the incident ends of the light guides of the connected endoscope and the reference endoscope is changed, it is possible to emit illumination light that has been corrected so as to have the predetermined color balance according to the area ratio.

The above-described aspect may further include a storage unit that stores correction values based on the ratio of the area of the incident end of the light guide provided in the reference endoscope and the area of the incident end of the light guide provided in the connected endoscope, wherein the adjustment unit may correct the color balance on the basis of the correction values stored in the storage unit.

By doing so, because the correction values corresponding to the connected endoscope are read from the storage unit, and the color balance is corrected, even when a different endoscope is connected, illumination light emitted from the distal end of the endoscope can be easily and rapidly made into illumination light having the predetermined color balance.

The above-described aspect may further include a detection unit that detects the type of a connected endoscope; and a calculation unit that calculates the area ratio of the incident end of the light guide provided in the endoscope detected by the detection unit, with respect to the incident end of a light guide that serves as a reference light guide, wherein the adjustment unit may increase the light amount of any of the surface light sources that has a smaller light-emitting area than the area of the incident end of the reference light guide, when the area ratio calculated by the calculation unit is greater than 1.

By doing so, the type of the connected endoscope is detected by the detection unit, and the area ratio of the incident end of the light guide in the detected endoscope and the incident end of the reference light guide is calculated by the calculation unit. When the area of the light guide in the connected endoscope is larger than the area of the incident end of the light guide in the reference endoscope, light from the surface light source that has a larger light-emitting area than the area of the incident end of the reference light guide enters the light guide. Therefore, the light amount from the surface light source that has a smaller light-emitting area than the area of the incident end of the reference light guide is increased, thereby making it possible to achieve the predetermined color balance.

The above-described aspect may further include a detection unit that detects the type of a connected endoscope; and a calculation unit that calculates the area ratio of the incident end of the light guide provided in the endoscope detected by the detection unit, with respect to the incident end of a light guide that serves as a reference light guide, wherein the adjustment unit increases the light amount of any of the surface light sources that has a larger light-emitting area than the area of the incident end of the reference light guide, when the area ratio calculated by the calculation unit is less than 1.

By doing so, the type of the connected endoscope is detected by the detection unit, and the area ratio of the incident end of the light guide in the detected endoscope and the incident end of the reference light guide is calculated by the calculation unit. When the area of the light guide in the connected endoscope is smaller than the area of the incident end of the light guide in the reference endoscope, the amount of light entering the light guide from the surface light source that has a larger light-emitting area than the area of the incident end of the reference light guide is reduced. Therefore, the light amount from the surface light source that has a larger light-emitting area than the area of the incident end of the reference light guide is increased, thereby making it possible to achieve the predetermined color balance.

REFERENCE SIGNS LIST 1 light source device
2, 3, 4, 5 LED (surface light source)
6 light-source optical system (multiplexing unit)
7 adjustment unit
16 ID reader (detection unit)
17 memory (storage unit)
18 endoscope
19 light guide

The invention claimed is:

1. A light source device comprising:
a plurality of surface light sources having different wavelength bands;
a multiplexing unit that multiplexes light beams emitted from the surface light sources; and
an adjustment unit that adjusts, when an endoscope that serves as a reference endoscope is connected, light-emission amounts of the surface light sources such that illumination light emitted from the reference endoscope has a predetermined color balance, and that adjusts, when an arbitrary endoscope is connected, the light-emission amounts of the surface light sources on the basis of the ratio of the color balance of illumination light emitted from the connected endoscope and the color balance of illumination light emitted from the reference endoscope.

2. A light source device according to claim 1, further comprising a storage unit that stores correction values based on the ratio of the color balance of illumination light emitted from the reference endoscope and the color balance of illumination light emitted from the connected endoscope,
wherein the adjustment unit adjusts the light-emission amounts of the surface light sources on the basis of the correction values stored in the storage unit.

3. A light source device according to claim 1, wherein the adjustment unit adjusts the light-emission amounts of the surface light sources on the basis of the ratio of the area of an incident end of a light guide provided in the reference endoscope and the area of an incident end of a light guide provided in the connected endoscope.

4. A light source device according to claim 3, further comprising a storage unit that stores correction values based on the ratio of the area of the incident end of the light guide provided in the reference endoscope and the area of the incident end of the light guide provided in the connected endoscope,
wherein the adjustment unit adjusts the light-emission amounts of the surface light sources on the basis of the correction values stored in the storage unit.

5. A light source device according to claim 3, further comprising:
a detection unit that detects the type of a connected endoscope; and
a calculation unit that calculates the area ratio of the incident end of the light guide provided in the endoscope detected by the detection unit, with respect to the incident end of a light guide that serves as a reference light guide, wherein the adjustment unit increases the light amount of any of the surface light sources that has a smaller light-emitting area than the area of the incident end of the reference light guide, when the area ratio calculated by the calculation unit is greater than 1.

6. A light source device according to claim 3, further comprising:

a detection unit that detects the type of a connected endoscope; and a calculation unit that calculates the area ratio of the incident end of the light guide provided in the endoscope detected by the detection unit, with respect to the incident end of a light guide that serves as a reference light guide, wherein the adjustment unit increases the light amount of any of the surface light sources that has a larger light-emitting area than the area of the incident end of the reference light guide, when the area ratio calculated by the calculation unit is less than 1.

* * * * *